Oct. 12, 1971 S. McGREDY Plant Pat. 3,071
ROSE PLANT
Filed Nov. 17, 1969
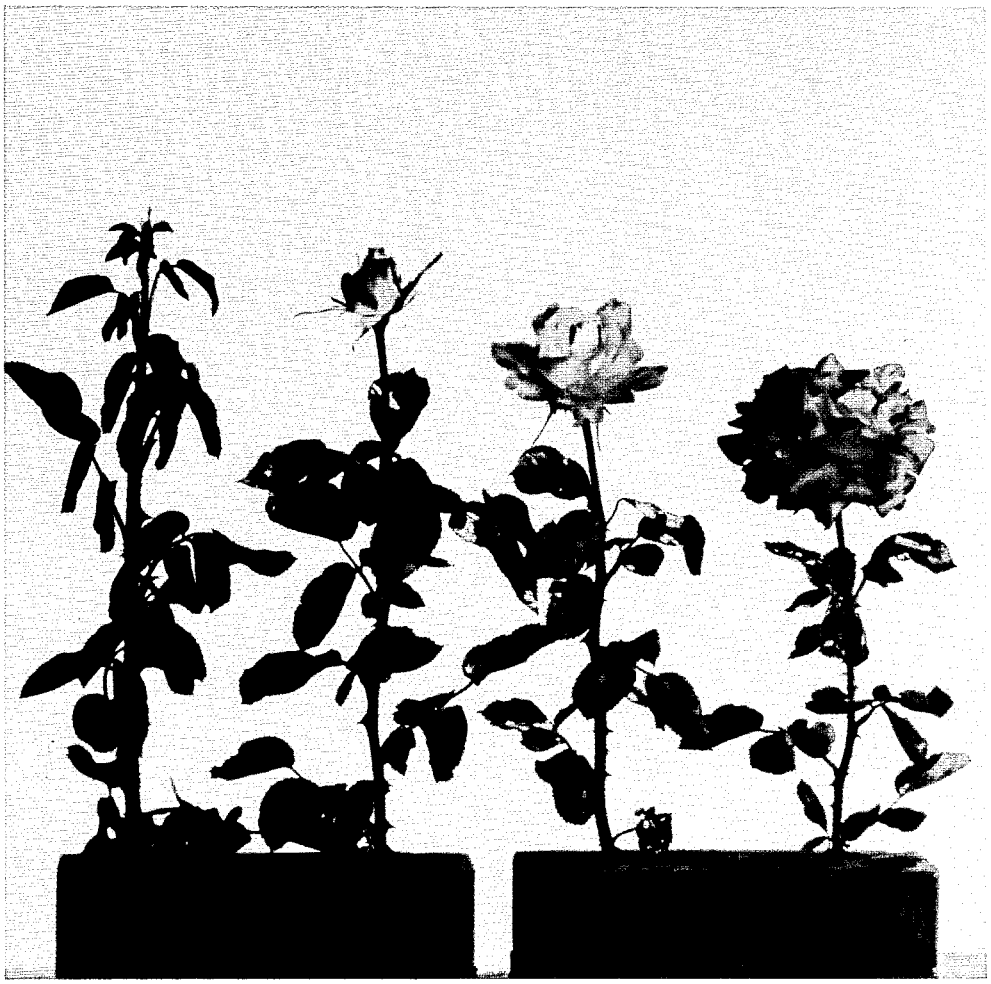

United States Patent Office

Plant Pat. 3,071
Patented Oct. 12, 1971

3,071
ROSE PLANT

Samuel McGredy, S. McGredy & Son Ltd.,
Portadown, Ireland

Filed Nov. 17, 1969, Ser. No. 877,534
Int. Cl. A01h 5/00
U.S. Cl. Plt.—12 1 Claim The invention relates to a new and distinct variety of rose plant of the hybrid tea class, originated by me in 1961 as a consequence of a breeding program begun in 1961. The parentage of my new rose plant is as follows: Perfecta × Piccadilly.

The object of the cross was to combine the free flowering habit of Piccadilly with a stronger plant on less fading bloom color. These objectives were achieved along with other desirable improvements, as evidenced by the following unique combination of characteristics which are outstanding in the new variety and which distinguish it from its parents, as well as from all other varieties of which I am aware. My new variety is primarily characterized by: The plant is stiffer and more upright than Piccadilly with extremely vigorous Crimson Red shoots produced from the base of the plant in great profusion, the color combination, while similar to Piccadilly when young, turns from Scarlet and yellow bicolor to deep Crimson rather than paling off. Apart from the heavily veined foilage, the plant bears little similarity to Perfecta.

Asexual reproduction of my new variety by budding, through a series of annual propagations at Santa Rosa, Calif., and Portland, Oreg., shows that all characteristics of the variety come true to form through succeeding propagations. The accompanying photographs illustrate the primary characteristics of my new variety as nearly true as is reasonably possible to make them with presently available techniques. The color references cited are those of the Horticultural Color Charts of the Royal Horticultural Society.

The following botanical description is based upon observation of field grown plants in Santa Rosa, Calif., and Portland, Oreg.

A vigorous shrub that easily reaches 90 cm. or more at maturity with a width of 40 cm. or more. The branching is moderate to light with strong ascending canes having an average diameter of 0.6 cm. The cane color at maturity is Willow Green (HCC 000862/1) and is heavily shot with Oxblood Red (HCC 00823) with imature or near the blooming apex. The thornation is moderate with 7–10 major thorns per internode toward the base of the plant having a reduced frequency towards the plant apex. There are minute, scattered prickles that increase in frequency, especially on the peduncles. The prickles and new thorns are Oxblood Red (HCC 00823/3) and are brownish when mature. The major thorns are hooked, abruptly tapered, having a base length of about 1.2 cm. with a profusion of about 0.8 cm. The internode length is 8–9 cm.

The foliage is abundant, glossy, leathery, and odd-pinnate with 3–5 leaflets being common. The overall leaf length varies with an average of 12 cm. in a 5 leaflet leaf. The apical leaflet is usually 6.5 cm. long by 5.25 cm. wide.

The leaflets are ovate, apiculate, doubly serrate, with light pubescence and prickles on the lower surface of the midrib. The upper surface of the leaflet is Sage Green (HCC 000861) and the lower surface is Willow Green (HCC 000862/1) anastamosed with Willow Green (HCC 000862/2), when immature, the leaflets are shot variously with Oxblood Red (HCC 000823) along with the petioles and rachis. The leaflets can be convoluted in surface configuration. The petiole is ribbed and winged with wings that persist, although reduced, to maturity. The wings are scarious, connate one-half to full length of petiole and are moderately apically appendaged. The rachis is also ribbed and has small thorns and prickles on its lower surface.

The inflorescence is solitary with a cup-shaped flower. The bud is pointed becoming urceolate to cup-shaped as it opens. The guard petals are Uranium Green (HCC 63/3) at the base and are heavily spotted with Dahlia Purple (HCC 931) and Cherry (HCC 722). The inner petals are Orange Buff (HCC 507/2) with Chrysanthemum Crimson (HCC 824/1) on the inner surface and Cherry (HCC 722) and Dahlia Purple (HCC 931) streaked or spotted lightly on the outer surface. The open flower is 4 cm. across, and 2–2½ cm. deep with 28–36 petals on the average and 10–15 petaloids. The petals are crisp, velvety, imbricated, obovate with entire to slightly dissected margins. The petal size ranges around 4 cm. wide by 3.75 cm. long. The petal base is Canary Yellow (HCC 2) fading to Canary Yellow (HCC 2/2) on the inner surface and is Barium Yellow (HCC 503) on the outer surface. The outer surface is Orange Buff (HCC 507/2) for the outer ⅔ of the petal surface with margins of Jasper Red (HCC 018/1) and some spots and streaks of Cherry (HCC 722) on the outer petals. The inner surface is Carmine (HCC 21) anastamosed with Cherry (HCC 722) on the outer ⅔ of the petal surface. The sepals are moderately to dramatically appendaged, both apically and laterally. The sepals are ciliate, truncate, lanceolate, pubescent within and glabrous without. Sepal color is Lettuce Green (HCC 861/3), shot heavily with Oxblood Red (HCC 00823) on the outside. The hypanthium is funnel form becoming urceolate, Lettuce Green (HCC 861/3), glabrous without and pubescent within. The disk is Yellow and well developed. Stamens number 125–150 with cream pink filaments and yellow anthers. Pistils number about 40–45 with reddish styles and light Yellow-Green stigmas.

The plant is mildew and disease resistant with no appreciable fragrance.

Having thus disclosed my invention, I claim:

1. A new and distinct variety of rose plant of the hybrid tea class substantially as herein shown and described primarily characterized by: the tall uprght plant allied to the freely produced dark Crimson new shoots; the scarlet and gold bicolor of the blooms turning Crimson with age; the heavily veined deep red foliage turning dark green when mature.

No references cited.

ROBERT E. BAGWILL, Primary Examiner